US012138327B2

(12) United States Patent
Battermann et al.

(10) Patent No.: US 12,138,327 B2
(45) Date of Patent: Nov. 12, 2024

(54) PROCESS FOR THE PREPARATION OF A READY-TO-USE, COSMETIC, FLOWABLE DETERGENT

(71) Applicant: Henkel AG & Co. KGaA, Duesseldorf (DE)

(72) Inventors: Marlene Battermann, Hamburg (DE); Sylvia Kerl, Hamburg (DE); Heike Schelges, Duesseldorf (DE); Sameh Hasan Fares, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 17/537,635

(22) Filed: Nov. 30, 2021

(65) Prior Publication Data

US 2022/0168191 A1 Jun. 2, 2022

(30) Foreign Application Priority Data

Nov. 30, 2020 (DE) .......................... 102020215078.8

(51) Int. Cl.
*A61K 8/02* (2006.01)
*A61K 8/41* (2006.01)
*A61K 8/46* (2006.01)
*A61Q 5/02* (2006.01)
*A61Q 19/10* (2006.01)

(52) U.S. Cl.
CPC .............. *A61K 8/022* (2013.01); *A61K 8/416* (2013.01); *A61K 8/463* (2013.01); *A61Q 5/02* (2013.01); *A61Q 19/10* (2013.01); *A61K 2800/80* (2013.01)

(58) Field of Classification Search
CPC .... A61K 8/022; A61K 8/44; A61K 2800/596; A61K 8/46; A61Q 5/02; A61Q 5/12; A61Q 5/00; A61Q 19/10; A61Q 19/00
See application file for complete search history.

(56) References Cited

U.S. PATENT DOCUMENTS

2019/0029936 A1* 1/2019 Bradt .................. A61K 8/9789
2021/0128415 A1* 5/2021 Stern ................ A45D 40/0087

FOREIGN PATENT DOCUMENTS

| CN | 106038352 A | 10/2016 |
| DE | 202011110839 U1 | 9/2016 |
| WO | 2010077627 A2 | 7/2010 |
| WO | 2019023332 A1 | 1/2019 |

OTHER PUBLICATIONS

Preliminary Search Report, FR2112367, Completed: Apr. 27, 2023; 6 pages.
Mintel, Macadamia Orange Shampoo Powder, Global New Products Database, Jun. 25, 2024, pp. 1-2, www.gnpd.com.

\* cited by examiner

*Primary Examiner* — Nicole P Babson
*Assistant Examiner* — John P Nguyen
(74) *Attorney, Agent, or Firm* — P. Scott Smith

(57) ABSTRACT

A process for the preparation of a ready-to-use cosmetic, flowable cleaning agent, in which a powdered surfactant mixture is mixed with water in a specific weight ratio is described herein. A flowable cleaning agent obtainable by the process is also described.

14 Claims, No Drawings

PROCESS FOR THE PREPARATION OF A READY-TO-USE, COSMETIC, FLOWABLE DETERGENT

FIELD OF THE INVENTION

The application describes a method for the preparation of a ready-to-use, cosmetic, flowable cleaning agent, in which a powdered surfactant mixture is mixed with water in a specific weight ratio. The application further describes a flowable cleaning agent obtainable by the process.

BACKGROUND OF THE INVENTION

Surfactant-containing products for cleaning the human body and hair have been known for a long time and are mainly sold as foam baths, shower preparations, shampoos and/or oral care compositions in liquid or paste form in suitable packaging. End users take the required amount of product from the packaging during use and dispose of it after emptying. Compared to classic soaps that are sold in solid form, such products offer the user the advantage of easy and quick handling, which is why they dominate the market today. However, this advantage is achieved by accepting certain disadvantages, which are discussed below. In most cases, the packaging of the described products in liquid or paste form consists of non-recyclable plastic, which is a serious problem from an environmental standpoint in view of the constantly growing amount of plastic waste.

Another problem is that previous products usually contained higher quantities of water or water/solvent mixtures, which means that the products have a larger volume and, possibly of greater importance from a transport point of view, a relatively high weight. This is disadvantageous for several reasons. In times of increasing water scarcity, resources should be saved. An undesirable, increased transport volume associated with large-volume heavy products is also important from an environmental and cost perspective. Another interesting point is that worldwide travel activity is constantly increasing. Consumers are therefore increasingly interested in cosmetic products that are easy to transport due to their low weight and volume. This is particularly relevant with regard to air travel, as larger containers containing liquids are generally excluded from being carried in an aircraft cabin, so that a passenger travelling only with hand luggage often finds himself in the situation, due to the cosmetics products that dominate the market today, of not being able to take his preferred product selection with him or having to decant the corresponding products into smaller containers first, which, however, is generally accompanied by an even greater volume of packaging material.

Providing alternative product forms with very low water content, contained in more environmentally friendly, recyclable packaging to save space, is therefore an important goal in the formulation of improved, contemporary and sustainable cosmetic products.

WO 2019/023332 discloses shampoos in powder form containing substantially sulphate-free surfactants (and other surfactants) and thickening and conditioning agents. The powders are rubbed between the hands under water and form a foam that is distributed on the hair. For the consumer, such a form of application is unfamiliar and possibly unwanted.

In addition, such a form of application can also have disadvantages, because depending on how vigorously a consumer rubs the powder and/or the amount of water used for lathering during the rubbing process, the resulting amount of lather and thus the effective amount of shampoo applied to the hair can vary greatly. In addition, with this type of application there is always the risk that some of the powder will not be lathered up, will clump in the consumer's wet hands and fall to the floor unused, or will be rinsed out of the hair unused after the foam has been massaged in.

BRIEF SUMMARY OF THE INVENTION

In view of the problems and requirements described above, the inventors have therefore set themselves the task of developing a process for cleaning the human body and/or hair in which sustainable, alternative product forms can be used flexibly, and in which, in addition to cleaning, excellent care of the human body and/or hair is also ensured.

The task of the invention is solved by the formulations, methods and uses described in detail below:

1. A method for the preparation of a ready-to-use, cosmetic, flowable cleansing composition comprising the following steps Providing a powder that is
   a. 40.0 to 80.0 wt. % of at least one anionic surfactant,
   b. 10.0 to 30.0 wt. % of at least one amphoteric and/or zwitterionic surfactant and
   c. 0.1 to 7.5 wt. % of at least one skin and/or hair-conditioning active ingredient, Mixing the powder with water in a weight ratio of 1:3 to 1:20, If necessary, shake or stir the resulting mixture until homogeneity.

2. The method of item 1, wherein the powder is mixed with water in a weight ratio of 1:4 to 1:15, preferably from 1:5 to 1:12 and in particular of 1:6 to 1:10.

3. The method according to one of the points 1 or 2, wherein the powder includes, based on its total weight, 45.0% to 75.0% by weight, preferably 50.0% to 70.0% by weight and particularly preferably 55.0% to 65.0% by weight of at least one anionic surfactant a).

4. The method according to any one of the preceding points, wherein the powder includes an amino acid-based surfactants, isethionates and/or alkyl sulphates.

5. The method as disclosed above, wherein the powder includes 11.0% to 28.0% by weight, preferably 12.5% to 26.0% by weight and 15.0% to 25.0% by weight of at least one amphoteric and/or zwitterionic surfactant b).

6. The process according to any one of the preceding points, wherein the powder includes at least three skin- and/or hair-conditioning active ingredients c) selected from the groups of Refatting agents and/or lipids,
   Emollients,
   Moisturizers,
   Vitamins, vitamin derivatives and/or vitamin precursors,
   Cationic polymers and/or
   Anti-dandruff active ingredients.

7. The process according to point 6, wherein the powder includes as active ingredients c) lipids, vegetable oils, butters and/or waxes, vitamins, vitamin precursors and/or vitamin derivatives, fatty acid esters and/or anti-dandruff active ingredients.

8. The process according to one of the preceding points, wherein the powder includes—based on its total weight—a maximum of 4% by weight of fillers and/or binders.

9. A cosmetic flowable cleansing composition obtainable by a process according to any one of the preceding points.

10. Cosmetic flowable detergent according to item 9, having a viscosity in the range of 1000 to 15000 mPas (Haake VT 550 UPM? Please add!/20° C.).

11. Use of a powder which is includes
  a. 40.0 to 80.0 wt. % of at least one anionic surfactant,
  b. 10.0 to 30.0 wt. % of at least one amphoteric and/or zwitterionic surfactant and
  c. 0.1 to 7.5 wt. % of at least one skin- and/or hair-conditioning active ingredient,
  for the production of a ready-to-use, cosmetic, flowable cleaning agent.

12. Use according to item 11, wherein the powder is mixed with water in a weight ratio of 1:3 to 1:20.

13. Cosmetic method for cleaning the human body and/or hair, in which a ready-to-use, cosmetic, flowable cleansing agent according to one of points 9 or 10 is distributed on the body part to be cleaned and rinsed off with water after a contact time of 10 seconds to 15 minutes.

DETAILED DESCRIPTION OF THE INVENTION

Accordingly, a first object of the present invention is a process for preparing a ready-to-use, cosmetic, flowable cleansing composition comprising the following steps.
  Providing a powder that is—based on its total weight—
    a. 40.0 to 80.0 wt. % of at least one anionic surfactant,
    b. 10.0 to 30.0 wt. % of at least one amphoteric and/or zwitterionic surfactant and
    c. 0.1 to 5.0 wt. % of at least one skin- and/or hair-conditioning active ingredient,
  Mixing the powder with water in a weight ratio of 1:3 to 1:20,
  if necessary, shake or stir the resulting mixture until homogeneity.
The previously defined method has the following advantages:
  The starting material used is a powder that can be produced in an energy-saving way and can be contained in more environmentally friendly manner, for example recyclable, packaging to save space,
  due to the high concentrations of active substances in the powder, few resources are consumed in its transport, and it can be easily transported without great effort or restrictions,
  the powder can be mixed with water from the tap by any user to produce the ready-to-use detergent,
  the powder dissolves very well in water,
  the mixing of the powder with water can be done in any (recyclable) container, such as a sealable glass bottle,
  the user can freely determine the volume of the ready-to-use cleaning preparation produced (and—depending on the quantities of powder and water selected—produce any quantity from a single portion to a supply of several liters).

By the method according to the invention, ready-to-use cosmetic, flowable cleaning agents of particularly pleasant and user-friendly consistency can be produced when the powder is mixed with water in a weight ratio of 1:3 to 1:20. A weight ratio of powder to water of 1:4 to 1:15, more preferably from 1:5 to 1:12 and in particular of 1:6 to 1:10. In a first preferred embodiment of the method according to the invention, the powder is mixed with water in a weight ratio of 1:4 to 1:15, more preferably from 1:5 to 1:12 and in particular of 1:6 to 1:10.

The powder used in the method according to the invention comprises, as a first essential ingredient, from 40.0 to 80.0% by weight of at least one anionic surfactant (based on the total weight of the powder).

Anionic surfactants exhibit excellent foaming and/or cleaning behavior, they are predominantly highly water-soluble and available in solid form. The following anionic surfactant types are suitable for use in the powders suitable for the method according to the invention:
  Ether carboxylic acids of the formula R—O—(CH2-CH2O)x-CH2-COOH, in which R is a linear or
    a. is a branched, saturated or unsaturated alkyl group with 8 to 30 C atoms and x=0 or 1 to 16,
    b. Surfactants available from natural sources such as
      Acylglycinate,
      Acyl sarcosinate,
      Acyl lactylates,
      Acylglutamates,
      Acylaspartate,
      Acyltaurates,
      Acylisethionates,
      Sulphosuccinates and
      the corresponding salified forms of the above-mentioned surfactants, the acyl groups comprising from 10 to 30 carbon atoms.
    c. Alpha-olefin sulphonates with 8 to 24 C atoms (alpha-olefin sulphonate surfactants),
    d. Alkyl sulphates of the formula R—O—SO3X, in which R is preferably a straight or branched chain,
    e. is a saturated or unsaturated alkyl group with 8 to 30 C atoms and X is an alkali metal, alkaline earth metal, ammonium or alkanol amine ion,
    f. Sulfonates of unsaturated fatty acids with 8 to 24 C-atoms and 1 to 6 double bonds,
    g. Esters of tartaric acid and citric acid with alcohols which are addition products of about 2-15 molecules of ethylene oxide and/or propylene oxide to fatty alcohols with 8 to 22 C atoms, and/or
    h. Alkyl and/or alkenyl ether phosphates of the formula

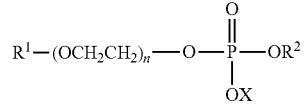

in which R1 is preferably an aliphatic hydrocarbon radical having 8 to 30 carbon atoms, R2 is hydrogen, a radical (CH2CH2O)nR1 or X, n is numbers from 0 to 10 and X is hydrogen, an alkali metal or alkaline earth metal or the group —NR3R4R5R6, where R3 to R6 independently of one another are a C1 to C4 hydrocarbon radical.

Particularly preferred are anionic surfactants from the aforementioned group b), as well as their corresponding salified forms, in which the acyl groups comprise 10 to 24 carbon atoms and in particular 10 to 18 carbon atoms.

Examples of particularly suitable anionic surfactants from group b) are alkali metal, alkaline earth metal and/or alkanolamine salts of so-called amino acid-based surfactants such as Cocoyl Glycinate, Cocoyl Sarcosinate, Lauroyl Sarcosinate, Myristoyl Sarcosinate, Oleyl Sarcosinate, Cocoyl Glutamate, Lauroyl Glutamate, stearoyl glutamate, lauroyl aspartate, palmitoyl aspartate, (C1-C4 alkyl) cocoyl taurate, (C1-C4 alkyl) lauroyl taurate, (C1-C4 alkyl) oleyl taurate and lauroyl lactylate, stearoyl lactylate, (C1-C4 alkyl) cocoyl isethionate, (C1-C4 alkyl) lauroyl isethionate, lauryl sulphosuccinate and/or any mixtures thereof.

Acylglutamates and/or acyl isethionates are particularly preferred.

Furthermore, surfactants from group d) are particularly preferred, because C8-C30 alkyl sulphates form a fine-pored, stable foam in combination with water even in small application quantities and they are very well tolerated by the skin.

More preferred are C10-C24 alkyl sulphates and particularly preferred are C12-C18 alkyl sulphates because these anionic surfactants, also known as "coco sulphates", are obtained from natural coconut oil and are particularly suitable as ECOCERT-compliant ingredients for use in the powders used for the method according to the invention.

Alkali salts such as potassium or sodium salts of coco sulfates are particularly preferred. Sodium Coco Sulfate (SCS) is particularly preferred.

In a preferred embodiment, the powders suitable for use in the process according to the invention include—based on their total weight—45.0 to 75.0% by weight, preferably 50.0 to 70.0% by weight and particularly preferably 55.0 to 65.0% by weight of at least one anionic surfactant a).

Anionic surfactants from groups b) and d) have proven to be particularly effective for providing foam-strong and skin-compatible powders. Accordingly, amino acid-based surfactants, isethionates and/or alkyl sulphates are particularly preferred. In a particularly preferred embodiment, the powders suitable for use in the process according to the invention includes as anionic surfactant(s) a) amino acid-based surfactants, isethionates and/or alkyl sulphates.

Within this embodiment, alkyl sulphates are particularly preferred because they are mild, very well tolerated by the skin and they form a creamy foam that makes the care aspect tangible during cleansing. Furthermore, alkyl sulphates can be produced on a purely vegetable basis and are also suitable for vegan cosmetics. Fatty acids of coconut oil can preferably serve as a raw material source.

In a further preferred embodiment, the powders suitable for use in the method according to the invention include—based on their total weight—20 to 80% by weight of at least one alkyl sulphate, preferably at least one compound known under the INCI designation sodium coco sulphate, and optionally further anionic surfactants mentioned above, preferably amino acid-based surfactants and/or isethionates.

The powder used in the method according to the invention comprises, as a second essential ingredient, from 10.0 to 30.0% by weight of at least one amphoteric and/or zwitterionic surfactant (based on the total weight of the powder).

The content of amphoteric and/or zwitterionic surfactants can optimize the foam properties of the ready-to-use, flowable detergent, in particular its foam quality, stability and mildness or skin compatibility.

Suitable amphoteric and/or zwitterionic surfactants in the sense of the present invention are: alkyl betaines, alkylamidoalkyl betaines, alkylamphoacetates, alkylamphodiacetates, alkylamphopropionates, alkylamphodipropionates, alkylsultaines, alkylhydroxysultaines, alkylamine oxides, alkylamphoglycinates, alkyliminodiacetates, alkyliminodipropionates, alkylamphopropylsulphonates, alkylamphocarboxyglycinates and alkylamphocarboxypropionates.

Suitable alkyl betaines and/or alkylamidopropyl betaines preferably comprise C4-C24, more preferably C6-C18, particularly preferably C8-C14 alkyl chains, which may be linear or branched, linear chains being preferred. Cocamidopropyl betaine is particularly preferred.

Particularly suitable alkylamphodiacetates, alkylamphodiacetates, alkylamphopropionates or alkylamphodipropionates are sodium cocoamphodiacetate and disodium cocoo-amphodiacetate.

In a preferred embodiment, the powders suitable for use in the method according to the invention include—based on their total weight—11.0 to 28.0% by weight, preferably 12.5 to 26.0% by weight and particularly preferably 15.0 to 25.0% by weight of at least one amphoteric and/or zwitterionic surfactant.

For some embodiments, it may be advantageous if the powders used in the method according to the invention includes further surfactants in addition to surfactants a) and b). These can preferably be selected from the group of non-ionic surfactants.

Suitable non-ionic surfactants in the sense of the present invention are:
Amine oxides, for example the surfactants known under the INCI names Cocamine Oxide, Lauramine Oxide and/or Cocamidopropylamine Oxide and commercially available from various suppliers,
Fatty acid alkanolamides, in particular the compounds known under the INCI designation Cocoamide MEA,
Fatty alcohol alkoxylates (especially ethoxylates) with a C-chain length of 8 to 24, especially 10 to 20, and a degree of alkoxylation (ethoxylation degree) of 2 to 30, such as laureth-4,
Mixtures of alkyl(oligo)glucosides and fatty alcohols, for example, the commercially available product Montanov® 68,
Alkyl(oligo)glycoside. Suitable alkyl (oligo)glycosides can be selected from compounds of the general formula of RO-[G]x, in which [G] is preferably derived from aldoses and/or ketosis with 5-6 carbon atoms, preferably from glucose.

The index number x stands for the degree of oligomerization (DP), i.e. the distribution of mono and oligoglycosides. The index number x preferably has a value in the range from 1 to 10, particularly preferably in the range from 1 to 3, whereby it may not be an integer but a fractional number that can be determined analytically.

Particularly preferred alkyl (oligo)glycosides have a degree of oligomerization between 1.2 and 1.5. The radical R preferably represents at least one alkyl and/or alkenyl radical containing 4 to 24 carbon atoms.

Especially preferred alkyl (oligo)glycosides are the compounds known under the INCI designations Caprylyl/Capryl Glucosides, Decyl Glucosides, Lauryl Glucosides and Coco Glucosides.

The nonionic surfactant(s) may be used in the powder suitable for use in the method according to the invention, preferably in an amount of from 0.1 to 10.0% by weight, more preferably from 0.15 to 8.5% by weight, particularly preferably from 0.2 to 7.5% by weight and especially from 0.25 to 6.00% by weight, based on the total weight of the powder.

The powder used in the method according to the invention comprises, as a third essential ingredient, from 0.1 to 7.5% by weight of at least one skin- and/or hair-conditioning active ingredient (based on the total weight of the powder). Preferably, skin- and/or hair-conditioning active ingredients are used in a total amount of 0.2 to 6% by weight, more preferably of 0.3 to 5% by weight and in particular of 0.5 to 4% by weight in the powder (based on the total weight of the powder). For the purposes of the present invention, suitable skin- and/or hair-conditioning active ingredients are preferably understood to mean:
Refatting agents and/or lipids,
Emollients,
Moisturizers,
Vitamins, vitamin derivatives and/or vitamin precursors,
Cationic polymers and/or
Anti-dandruff agents.

Suitable refatting agents and/or lipids in the sense of the present invention are understood to be all fats and fat-like substances which preferably melt in the range of 30-150° C. These include triglycerides, mono- and/or diglycerides, waxes, fatty and wax alcohols, fatty acids, esters and/or ethers of fatty alcohols and fatty acids as well as fatty acid amides, hydrocarbons, lipoproteins, glycolipids, phospholipids or any mixtures of these substances. Triglycerides are understood to be "natural" oils, preferably vegetable oils. These preferably include triglycerides and mixtures of triglycerides such as amaranth seed oil, apricot kernel oil, argan oil, avocado oil, babassu oil, bamboo oil, baobab oil, canola oil, safflower oil, pomegranate seed oil, rosehip seed oil, hemp oil, hazelnut oil, red currant oil, black currant oil, jojoba oil, coconut oil, pumpkin seed oil, Macadamia nut oil, mallow oil, (sweet) almond oil, mango kernel oil, evening primrose oil, olive oil, Brazil nut oil, passion fruit oil, palm kernel oil, peach kernel oil, rambutan oil, rice bran oil, Castor Oil, Safflower Oil, Sasanqua Oil, Sesame Oil, Soybean Oil, Sunflower Oil, Tea Tree Oil, Grape Seed Oil, Tsubaki Oil, Walnut Oil, Wheat Germ Oil and/or Meadowfoam Oil.

Suitable plant butters preferably include shea butter, mango butter, murumuru butter, cocoa butter, apricot kernel butter, mafuri butter, bacuri butter, tucuma butter, ucuuba butter and/or cupuacu butter.

Waxes are natural or artificially obtained substances with the following properties: they are of solid to brittle hard consistency, coarse to fine crystalline, translucent to cloudy, and melt above 30° C. without decomposition. They are already low viscosity and non-fibrous a little above the melting point and show a strongly temperature-dependent consistency and solubility. Natural vegetable waxes with a melting point of 30-150° C., for example, can be used according to the invention, such as e.g. Candelilla wax, carnauba wax, Japan wax, esparto grass wax, cork wax, guaruma wax, rice germ oil wax, sugar cane wax, ouricury wax, montan wax, sunflower wax, fruit waxes such as orange waxes, lemon waxes, grapefruit wax, bayberry wax and animal waxes such as beeswax, shellac wax, spermaceti, lanolin and brushing fat. In the spirit of the invention, it may be advantageous to use hydrogenated or cured waxes. Natural waxes that can be used according to the invention also include mineral waxes, such as ceresin and ozokerite, or petrochemical waxes, such as petrolatum, paraffin waxes and microwaxes. Chemically modified waxes, in particular the hard waxes, such as montan ester waxes, sasol waxes and hydrogenated jojoba waxes, can also be used as wax components. Synthetic waxes which can be used according to the invention include, for example, waxy polyalkylene waxes and polyethylene glycol waxes.

Esters of glycerol with one or more straight-chain or branched, saturated or unsaturated C8-C30 fatty acids such as glyceryl palmitate, stearate or oleate can be used as mono- and/or diglycerides. A particularly preferred mono- and/or diglyceride is a compound known under the INCI name PCA Glyceryl Oleate, as well as glyceride mixtures, e.g. Cutina® HR (hardened castor oil) and Novata® AB (mixture of C12-C18 mono-, di- and triglycerides).

The fatty alcohols which can be used according to the invention include e.g. the unbranched C14-C50 fatty alcohols, in particular the C14-C30 fatty alcohols obtained from natural fats, oils and waxes, such as myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. Preferred according to the invention are unbranched, saturated and unsubstituted fatty alcohols. However, branched, saturated or unsaturated fatty alcohols can also be used according to the invention. Also usable according to the invention are fatty alcohol cuts, such as are produced during the reduction of naturally occurring fats and oils.

Preferred fatty acids are C12-C40 fatty acids or mixtures thereof. These include, for example, lauric, tridecanic, myristic, pentadecanic, palmitic, margaric, stearic, nonadecanic, arachic, behenic, lignoceric, cerotinic, melissic, erucic and elaeostearic acids, as well as substituted fatty acids such as 12-hydroxystearic acid. Such as 12-hydroxystearic acid, and the amides or monoethanolamides of the fatty acids, this list being exemplary and not restrictive.

Suitable hydrocarbons are understood to be liquid or solid hydrocarbons such as petrolatum, ceresin, ozokerite, paraffins, isoparaffins and/or squalene.

Suitable glycolipids in the sense of the present invention are sugar surfactants, alkyl polyglycosides and/or ceramides. A suitable phospholipid in the sense of the present invention is lecithin.

Refatting agents and/or lipids may be used in the powder suitable for use in the method according to the invention—based on the total weight of the powder—in amounts of 0.01 to 5% by weight, more preferably 0.05 to 4.5% by weight and particularly preferably 0.1 to 4% by weight.

Emollients suitable according to the invention are preferably waxes, wax alcohols, fatty acids and esters of fatty alcohols and fatty acids, as already described earlier in this application.

Suitable moisturizers in the sense of the present invention can preferably be selected from
  Polyols such as glycerol,
  Lactic acid and or derivatives and/or salts thereof, and
  Trimethylglycine.
They can be used in the powder suitable for use in the method according to the invention—based on the total weight of the powder—in amounts of 0.01 to 4% by weight, more preferably 0.05 to 3% by weight and particularly preferably 0.1 to 2% by weight.

By suitable "vitamins, vitamin derivatives and/or vitamin precursors" is preferably meant:
  Vitamin A: the group of substances known as vitamin A includes retinol (vitamin A1) and 3,4-didehydroretinol (vitamin A2). The β-carotene is the provitamin of retinol. Vitamin A components include vitamin A acid and its esters, vitamin A aldehyde and vitamin A alcohol and its esters such as palmitate and acetate.
  Vitamin B: the vitamin B group or vitamin B complex includes
  Vitamin B1 (Thiamine)
  Vitamin B2 (Riboflavin)
  Vitamin B3. The compounds nicotinic acid and nicotinamide (niacinamide) are frequently listed under this designation.
  Vitamin $B_5$ (pantothenic acid and panthenol). Within this group, panthenol is preferred. Usable derivatives of panthenol are in particular the esters and ethers of panthenol, pantolactone and cationically derivatized panthenols. Individual representatives include panthenol triacetate, panthenol monoethyl ether and its monoacetate and cationic panthenol derivatives.
  Vitamin $B_6$ (pyridoxine as well as pyridoxamine and pyridoxal).

Vitamin C (ascorbic acid): use in the form of palmitic acid ester, glucosides or phosphates may be preferred. Use in combination with tocopherols may also be preferred.

Vitamin E (tocopherols, especially α-tocopherol).

Vitamin F: the term "vitamin F" usually refers to essential fatty acids, especially linoleic acid, linolenic acid and arachidonic acid.

Vitamin H: Vitamin H is the compound (3aS,4S,6aR)-2-oxohexahydrothienol[3,4-d]-imidazole-4-valeric acid, for which the trivial name biotin has since become established.

Particularly preferred are vitamins, provitamins and vitamin precursors from groups A, B, E and H. Very particularly preferred are nicotinamide, tocopherol, pantolactone and/or panthenol; especially preferred are nicotinamide, tocopherol and/or panthenol. Vitamins, vitamin derivatives and/or vitamin precursors may be used in the powder suitable for use in the process according to the invention—based on the total weight of the powder—preferably in amounts of 0.001 to 1% by weight, more preferably 0.002 to 0.75% by weight and particularly preferably 0.005 to 0.5% by weight.

Suitable cationic polymers within the meaning of the present invention are preferably understood to be cationic polymers of natural origin, in particular cationic polysaccharide polymers. Particularly suitable examples are:

- quaternized cellulose derivatives, as referred to under the names Celquat® and Polymer JR® are available on the market,
- cationic starch derivatives, such as those commercially available under the name Mirustyle®,
- hydrophobically modified cellulose derivatives, such as the cationic polymers sold under the trade name Soft-Cat®,
- cationic alkyl polyglycosides,
- cationised honey, for example the commercial product Honeyquat® 50,
- cationic guar derivatives, such as in particular the products marketed under the trade names Cosmedia® Guar N-Hance® and Jaguar®.
- cationic cassia and/or inulin derivatives such as those listed under the INCI designation Cassia Hydroxypropyltrimonium Chloride and Hydroxypropyltrimonium Inulin known cationic polymers.

Cationic polymers can be used in the powder suitable for use in the process according to the invention—based on the total weight of the powder—preferably in amounts of 0 to 4% by weight, more preferably 0.1 to 3.0% by weight and in particular 0.15 to 2.0% by weight.

For the purposes of the present invention, suitable anti-dandruff agents include piroctone olamine, climbazole, zinc pyrithione, ketoconazole, salicylic acid, sulfur, selenium sulfide, tar preparations, undecenic acid derivatives, burdock root extracts, poplar extracts, nettle extracts, walnut shell extracts, birch extracts, willow bark extracts, rosemary extracts, arnica extracts and/or propanediol caprylates. Preferred powders suitable for use in the method according to the invention are natural anti-dandruff actives such as the aforementioned plant extracts and/or anti-dandruff actives accessible from natural sources such as propanediol caprylates. The proportion by weight of anti-dandruff agents in the total weight of the powder is preferably 0.01 to 5% by weight, preferably 0.025 to 4% by weight and in particular 0.05 to 3% by weight.

In a particularly preferred embodiment, the powder to be used in the method according to the invention include at least one to three skin and/or hair-conditioning active ingredients c) from the groups of the

- Refatting agents and/or lipids,
- Emollients,
- Moisturizers,
- Vitamins, vitamin derivatives and/or vitamin precursors,
- Cationic polymers and/or
- Anti-dandruff active ingredients.

Within this embodiment, it is particularly preferred that the powder include as active ingredients c) lecithin, vegetable oils, butters and/or waxes, vitamins, vitamin precursors and/or vitamin derivatives, fatty acid esters and/or anti-dandruff active ingredients.

Particularly preferred active ingredients c) are lecithin, apricot kernel oil, argan oil, avocado oil, rosehip kernel oil, hemp oil, jojoba oil, coconut oil, macadamia nut oil, (sweet) almond oil, olive oil, Brazil nut oil, peach kernel oil, castor oil, sunflower oil, grape seed oil, shea butter, Cocoa butter, PCA glyceryl oleate, carnauba wax, beeswax, ceramides, glycerin, lactic acid, trimethylglycine (betaine), nicotinamide, tocopherol, pantenol, biotin, cationic cellulose derivatives, cationic guar, cassia and/or inulin derivatives and/or propanediol caprylate.

To further increase the skin and/or hair conditioning properties, the powders to be used in the method according to the invention may additionally include protein hydrolysates and/or plant extracts.

Suitable protein hydrolysates are product mixtures that can be obtained by acidic, basic or enzymatic catalyzed degradation of proteins. Protein hydrolysates of vegetable, animal and/or marine origin can be used. Animal protein hydrolysates include elastin, collagen, keratin, silk and milk protein hydrolysates, which may also be in the form of salts. Such products are marketed under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda). Protein hydrolysates of vegetable origin are preferred, e.g. soy, almond, rice, pea, potato and wheat protein hydrolysates. Such products are available under the trademarks Gluadin® (Cognis), DiaMin® (Diamalt), Lexein® (Inolex) and Crotein® (Croda). Cationized protein hydrolysates can also be used, whereby the underlying protein hydrolysate can be derived from animals, for example from collagen, milk or keratin, from plants, for example from wheat, corn, rice, potatoes, soy or almonds, from marine life forms, for example from fish collagen or algae, or from biotechnologically produced protein hydrolysates. The protein hydrolysates underlying the cationic derivatives can be obtained from the corresponding proteins by chemical, especially alkaline or acid hydrolysis, by enzymatic hydrolysis and/or a combination of both types of hydrolysis. The hydrolysis of proteins usually results in a protein hydrolysate with a molecular weight distribution of about 100 Daltons up to several thousand Daltons. Preferred are those cationic protein hydrolysates whose underlying protein fraction has a molecular weight of 100 to 25000 Dalton, preferably 250 to 5000 Dalton. Furthermore, cationic protein hydrolysates are quaternized amino acids and mixtures thereof. Quaternization of the protein hydrolysates or amino acids is often carried out using quaternary ammonium salts such as N,N-dimethyl-N-(n-alkyl)-N-(2-hydroxy-3-chloro-n-propyl)-ammonium halides. Furthermore, the cationic protein hydrolysates can also be further derivatized (derived?). Typical examples of the cationic protein hydrolysates and derivatives are the products known under the INCI designations and commercially available: Cocodimonium Hydroxypropyl Hydrolyzed Collagen, Cocodimopnium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein. The percentage by weight of the protein hydrolysates in the total weight of the powder is preferably 0.01 to 3% by weight, more preferably 0.025 to 2% by weight and in particular 0.05 to 1% by weight.

Suitable plant extracts are mainly the extracts of green tea, oak bark, nettle, witch hazel, hops, henna, chamomile, burdock root, horsetail, hawthorn, linden blossom, almond, Aloe vera, spruce needle, horse chestnut, date palm, cinnamon tree, sandalwood, juniper, coconut, mango, apricot, lime, wheat, kiwi, melon, orange, grapefruit, sage, rosemary, birch, mallow, Valerian, Meadowfoam, Quender, Yarrow, Thyme, Melissa, Hauhechel, Coltsfoot, Marshmallow, Meristem, Ginseng, Coffee, Cocoa, Moringa, Ginger Root and Ayurvedic plant extracts such as *Aegle marmelos* (Bilwa), *Cyperus rotundus* (Nagar Motha), *Emblica officinalis* (Amalki), *Morida citrifolia* (Ashyuka), *Tinospora cordifolia* (Guduchi), *Santalum album*, (Chandana), *Crocus sativus* (Kumkuma), *Cinnamonum zeylanicum* and *Nelumbo nucifera* (Kamala), sweet grasses such as wheat, barley, rye, oats, spelt, corn, the different varieties of millet (panicle millet, Finger millet, foxtail millet as examples), sugarcane, ryegrass, meadow foxtail, smooth oats, bunchgrass, meadow fescue, pipegrass, bamboo, cotton grass, lampbush grasses, Andropogonodeae (*Imperata cylindrica* also called flame grass or cogon grass), buffalo grass, silt grasses, dogtooth grasses, love grasses, *Cymbopogon* (lemon grass), *Oryzeae* (rice), *Zizania* (wild rice), Beach oats, perennial oats, honey grasses, quaking grasses, meadow grasses, couch grasses, and *Echinacea*, especially *Echinacea angustifolia* DC, *Echinacea paradoxa* (Norton), *Echinacea simulata, E. atrorubens, E. tennesiensis, Echinacea strigosa* (McGregor), *Echinacea laevigata, Echinacea purpurea* (L.) Moench and *Echinacea pallida* (Nutt), all kinds of seaweeds, coral moss and seaweed (such as *Macrocystis pyrifera* extract), all kinds of vines and pericarp of *Litchie chinensis*.

Suitable extracts can be obtained from the fruits, seeds, flowers, roots, leaves and/or barks of the above plants or from the whole plants (algae, seaweed). According to the invention, the plant extracts can be used both in pure and diluted form. If they are used in diluted form, they usually include approx. 2-80% by weight of active substance and as solvent the extracting agent or extracting agent mixture used in their extraction. Suitable extraction agents are usually water and/or alcohols. The plant extract(s) may be used in the powder preferably in total amounts of 0.001 to 1% by weight, preferably 0.0025 to 0.75% by weight, and more preferably 0.05 to 0.5% by weight, the amounts being based on the weight of the powder.

The process according to the invention leads to ready-to-use, cosmetic, flowable cleaning agents in a fast and uncomplicated manner. Nowadays, users prefer natural, sustainable products that include as few to no synthetic ingredients as possible and/or ingredients that are not absolutely necessary for the respective application purpose. In the process according to the invention, therefore, powders are preferably used which do not comprise large quantities of other ingredients in addition to the mandatory and optional ingredients mentioned above (with the exception of agents for adjusting the pH value, preservatives, perfumes and/or inorganic salts such as sodium chloride). In a preferred embodiment, the powder used in the process according to the invention includes a maximum of 4% by weight—based on its total weight of fillers and/or binders.

A second object of the present invention is a cosmetic flowable cleansing composition obtainable by the process according to the invention. For the purposes of the present invention, "flowable" is preferably understood to mean a viscosity of the ready-to-use, cosmetic, flowable cleaning agent in the range from 500 to 30000 mPas, more preferably 500 to 25000 and in particular 1000 to 15000 mPas (measured with Haake VT 550 MVII/20° C.). A preferred embodiment of the second subject matter of the invention is characterized in that the ready-to-use cosmetic flowable cleansing composition has a viscosity in the range of 1000 to 15000 mPas (Haake VT 550 MVII/20° C.).

A third object of the invention is the use of a powder which is based on
 a) 40.0 to 80.0 wt. % of at least one anionic surfactant,
 b) 10.0 to 30.0 wt. % of at least one amphoteric and/or zwitterionic surfactant and
 c) 0.1 to 7.5 wt. % of at least one skin- and/or hair-conditioning active ingredient,
 d) for the production of a ready-to-use, cosmetic, flowable cleaning agent.

Within this embodiment, powders are preferred which are mixed with water in a weight ratio of 1:3 to 1:20 to form a ready-to-use, cosmetic, flowable cleaning agent.

A fourth object of the invention is a cosmetic process for cleaning the human body and/or hair, in which a ready-to-use, cosmetic, flowable cleaning composition of the second object of the invention is spread on the body part to be cleaned and rinsed off with water after an exposure time of 10 seconds to 15 minutes.

What has been said about the method according to the invention applies to the aforementioned means of the second object of the invention and the use of the third object of the invention.

EXAMPLES

Basic exemplary compositions for the powder to be used in the process according to the invention are shown in the following Tables 1-6 (compositions Z1 to Z21). Quantities refer to [% by weight] (unless otherwise stated):

TABLE 1

| Ingredient | Z1 | Z2 | Z3 | Z4 |
|---|---|---|---|---|
| (a): one or more anionic surfactant(s) | 40-80 | 45-75 | 50-70 | 55-65 |
| (b): one or more amphoteric and/or zwitterionic surfactant(s) | 10-30 | 11-28 | 12.5-26 | 15-25 |
| (c): one or more skin- and/or hair-conditioning active ingredients. | 0.1-7.5 | 0.2-6 | 0.3-5 | 0.5-4 |
| If necessary, other auxiliaries and additives | ad 100 | ad 100 | ad 100 | ad 100 |

TABLE 2

| Ingredient | Z5 | Z6 | Z7 | Z8 |
|---|---|---|---|---|
| (a): one or more anionic surfactant(s) | 40-80 | 45-75 | 50-70 | 55-65 |
| (b): one or more amphoteric and/or zwitterionic surfactant(s) | 10-30 | 11-28 | 12.5-26 | 15-25 |
| (c): one or more skin- and/or hair- conditioning active ingredients. | 0.1-7.5 | 0.2-6 | 0.3-5 | 0.5-4 |
| non-ionic surfactant | 0.1-10 | 0.15-8.5 | 0.2-7.5 | 0.25-6 |
| If necessary, other auxiliaries and additives | ad 100 | ad 100 | ad 100 | ad 100 |

TABLE 3

| Ingredient | Z9 | Z10 | Z11 | Z12 |
|---|---|---|---|---|
| (a): one or more anionic surfactant(s) | 40-80 | 45-75 | 50-70 | 55-65 |
| (b): one or more amphoteric and/or zwitterionic surfactant(s) | 10-30 | 11-28 | 12.5-26 | 15-25 |
| c): Replenishing agents and/or lipids, emollients, moisturisers, vitamins, vitamin derivatives and/or vitamin precursors, cationic polymers and/or anti-dandruff agents | 0.1-7.5 | 0.2-6 | 0.3-5 | 0.5-4 |
| If necessary, other auxiliaries and additives | ad 100 | ad 100 | ad 100 | ad 100 |

TABLE 4

| Ingredient | Z13 | Z14 | Z15 | Z16 |
|---|---|---|---|---|
| a): Amino acid-based surfactant, isethionate and/or alkyl sulphate | 40-80 | 45-75 | 50-70 | 55-65 |
| (b): one or more amphoteric and/or zwitterionic surfactant(s) | 10-30 | 11-28 | 12.5-26 | 15-25 |
| c): Replenishing agents and/or lipids, emollients, moisturisers, vitamins, vitamin derivatives and/or vitamin precursors, cationic polymers and/or anti-dandruff agents | 0.1-7.5 | 0.2-6 | 0.3-5 | 0.5-4 |
| non-ionic surfactant | 0.1-10 | 0.15-8.5 | 0.2-7.5 | 0.25-6 |
| If necessary, other auxiliaries and additives | ad 100 | ad 100 | ad 100 | ad 100 |

TABLE 5

| Ingredient | Z17 | Z18 | Z19 | Z20 |
|---|---|---|---|---|
| a): Amino acid-based surfactant, isethionate and/or alkyl sulphate | 40-80 | 45-75 | 50-70 | 55-65 |
| (b): one or more amphoteric and/or zwitterionic surfactant(s) | 10-30 | 11-28 | 12.5-26 | 15-25 |
| c): Lipids, vegetable oils, butters and/or waxes, vitamins, vitamin precursors and/or vitamin derivatives, fatty acid esters and/or anti-dandruff active ingredients. | 0.1-7.5 | 0.2-6 | 0.3-5 | 0.5-4 |
| non-ionic surfactant | 0.1-10 | 0.15-8.5 | 0.2-7.5 | 0.25-6 |
| If necessary, other auxiliaries and additives | ad 100 | ad 100 | ad 100 | ad 100 |

TABLE 6

| Ingredient | Z21 |
|---|---|
| Sodium Coco Sulfate | 55-65 |
| Cocamidopropyl betaine | 15-25 |
| Coco glucosides | 0.25-6 |
| Trimethylglycine | 0-7 |
| Lecithin | 0.01-5 |
| PCA Glyceryl Oleate | 0.01-5 |
| Argan oil | 0.01-5 |
| Perfume | 0.1-2 |

For example, a cosmetic powder according to Z21 was placed in a glass bottle. Subsequently, water (weight ratio powder:Water from 1:7) added, the glass bottle closed and shaken gently until the powder had completely dissolved.

The resulting shampoo was transparent to slightly cloudy. It was applied to the hair in the usual way and had the following benefits:
- excellent cleaning properties,
- high foam quantity,
- very good foam quality (fine-pored foam with excellent feel),
- good (clean, well-groomed) hair feeling in wet and dry hair,
- good rinsability,
- good hair grip,
- very good detangling and combability of wet hair,
- increased gloss,
- increased hair volume,
- increased suppleness.

What is claimed is:

1. A method for the preparation of a ready-to-use, cosmetic, flowable cleansing composition, comprising:
   providing a powder, said powder comprising:
   a) 40.0 to 80.0 wt. % of at least one anionic surfactant, wherein said anionic surfactant includes at least one alkyl sulfate C8-C30 alkyl sulfate or alkali salt thereof,
   b) 10.0 to 30.0 wt. % of at least one amphoteric and/or zwitterionic surfactant, and
   c) 0.1 to 7.5 wt. % of at least one skin- and/or hair-conditioning active ingredient
   mixing the powder with water in a ratio of 1:3 to 1:20.

2. The method of claim 1, wherein the powder is mixed with water in a weight ratio of 1:4 to 1:15.

3. The method of claim 1, wherein the powder is mixed with water in a weight ratio of 1:5 to 1:12.

4. The method of claim 1, wherein the powder is mixed with water in a weight ratio of 1:6 to 1:10.

5. The method according to claim 1, wherein the powder includes 45.0% to 75.0% by weight of at least one anionic surfactant a).

6. The method according to claim 1, wherein the powder includes 50.0% to 70.0% by weight of at least one anionic surfactant a).

7. The method according to claim 1, wherein the powder includes 55.0% to 65.0% by weight of at least one anionic surfactant a).

8. The method according to claim 1, wherein the powder includes an anionic surfactant selected from the group consisting of amino acid-based surfactants, isethionates and/or alkyl sulfates.

9. The method according to claim 1, wherein the powder includes 11.0% to 28.0% by weight of at least one amphoteric and/or zwitterionic surfactant b).

10. The method according to claim 1, wherein the powder includes 12.5% to 26.0% by weight of at least one amphoteric and/or zwitterionic surfactant b).

11. The method according to claim 1, wherein the powder includes 15.0% to 25.0% by weight of at least one amphoteric and/or zwitterionic surfactant b).

12. The method according to claim 1, wherein the powder includes at least three skin and/or hair conditioning active ingredients c) selected from the group consisting of:
   refatting agents and/or lipids,
   emollients,
   moisturizers,
   vitamins, vitamin derivatives and/or vitamin precursors,
   cationic polymers and/or
   anti-dandruff active ingredients.

13. The method according to claim 1, wherein the anionic surfactant is an alkali salt of a C12-C18 alkyl sulfate.

14. The method according to claim 1, wherein the anionic surfactant is sodium coco sulfate.

* * * * *